United States Patent [19]

Osband et al.

[11] Patent Number: 4,474,876

[45] Date of Patent: Oct. 2, 1984

[54] FLOW CYTOMETRIC ANALYSIS OF HISTAMINE RECEPTORS

[75] Inventors: Michael E. Osband, Brookline; Ellen B. Cohen, Needham, both of Mass.

[73] Assignees: Trustees of Boston University, Boston, Mass.; Smithkline Beckman Corporation, Philadelphia, Pa.

[21] Appl. No.: 319,659

[22] Filed: Nov. 9, 1981

[51] Int. Cl.³ .................... G01N 33/48; G01N 33/50; G01N 21/64
[52] U.S. Cl. .......................................... 435/4; 435/29; 435/810; 436/501; 436/503; 436/506; 436/507
[58] Field of Search .................... 435/4, 7, 29, 810; 436/501, 506, 507, 518, 519, 531, 532, 543, 544, 545, 546, 535, 503; 422/61

[56] References Cited

U.S. PATENT DOCUMENTS

| | | | |
|---|---|---|---|
| 3,988,115 | 10/1976 | Modabber | 435/7 |
| 4,061,466 | 12/1977 | Sjöholm et al. | 260/112 |
| 4,220,450 | 9/1980 | Maggio | 435/7 |
| 4,256,834 | 3/1981 | Zuk et al. | 435/7 |

OTHER PUBLICATIONS

Osband et al., "Biochemical Analysis of Specific Histamine H1 and H2 receptors on Lymphocytes", *Chem. Absts.,* vol. 95, No. 7, p. 306 (1981), Absts. No. 57537w.
Matthyssen et al., "Binding of Histamine and other Ligand Conjugated Macromolecules to Lymphocytes", *Chem. Absts.,* vol. 83, No. 7, p. 332 (1975), Absts. No. 56622k.
Rocklin, "Modulation of Cellular-Immune Responses in Vivo and in Vitro by Histamine Receptor-Bearing Lymphocytes", *J. Chem. Invest., vol. 57, No. 4 (1976), pp. 1051–1058.*

*Primary Examiner*—Sidney Marantz
*Attorney, Agent, or Firm*—Hamilton, Brook, Smith and Reynolds

[57] ABSTRACT

A method for analyzing cells to determine whether they have substantial numbers of H1 and H2 histamine receptors. Also an assay kit and a composition for conducting such analyses. The assays involve fluorescent polymeric molecules to which a plurality, preferably from about 30 to about 100, of histamine or histamine blocker molecules are attached. Procedures for optimizing several variables which are essential to effective and reliable determinations.

23 Claims, 5 Drawing Figures

FLOW CYTOMETRIC ANALYSIS OF HISTAMINE RECEPTORS

DESCRIPTION

Government Support

The invention described herein was supported in whole or in part by a grant from the National Institutes of Health.

TECHNICAL FIELD

This invention is in the fields of chemistry, biology and biochemistry.

BACKGROUND ART

Histamine is a biogenic amine with the following structural configuration:

Histamine is secreted by various types of cells, and it may become attached to receptors on the membranes of other cells. The attachment of histamines to histamine receptors can cause or aggravate a wide variety of physiological reactions, including vasodilation, bronchoconstriction, secretion of gastric acids, and skin hives [1]. The term "histamine" as used herein includes substituted forms of histamine, such as methyl histamine.

The effects of histamine may be mimicked by compounds that are referred to as agonists [2]. Histamine agonists include 2(2-pyridyl)ethylamine, dimaprit, and various substituted histamines, such as 4-methylhistamine. Histamine agonists mimic the effect of histamine by attaching to histamine receptors.

The effects of histamine may be blocked by compounds that are referred to as antagonists [3]. Histamine antagonists include diphenhydramine and cimetidine, which block various effects of histamine by attaching to histamine receptors without inducing the physiological effects caused by histamine. However, at high dosage levels, certain antagonists such as impromidine may cause agonistic effects on certain types of cells.

Histamine receptors are believed to be proteinous molecules with molecular weights in the range of 40,000 to 50,000 daltons. They are divided into at least two categories, designated as H1 receptors and H2 receptors [4]. Histamine will bind to either type of receptor. Certain antagonists such as diphenhydramine will bind to and consequently block H1 receptors to a much greater extent than they will block H2 receptors. Other antagonists, including cimetidine, will bind to H2 receptors to a much greater extent than they will block H1 receptors. It is believed that binding of histamine to H2 receptors plays an important role in the activation of gastric secretion. Therefore, H2 antagonists such as cimetidine are commonly used to treat ulcers by reducing gastric secretion [5]. It is believed that binding of histamine to H1 receptors plays an important role in skin hives and bronchioconstriction [6]. It is suspected that other categories of histamine receptors exist, which are not blocked by H1 blockers or by H2 blockers. For convenience, such receptors are referred to herein as H3 receptors.

When a histamine, histamine agonist, or histamine antagonist molecule binds to a histamine receptor, the reaction is referred to herein as specific binding. By comparison, if histamine (which is a somewhat reactive molecule) clings or binds to some other part of a cell, a test tube, a filter, or any other surface, such a reaction is referred to herein as non-specific binding.

Histamine blockers, as used herein, is a generic term comprising histamine agonists, histamine antagonists, and other molecules which are capable of specific binding with a histamine receptor, thereby preventing a histamine molecule from specifically binding to the blocked receptor. By comparison, antihistamines which react with histamine, rather than with histamine receptors are not regarded herein as histamine blockers. A histamine blocker which binds to H1 receptors with greater affinity than it binds to H2 receptors is referred to as an "H1 blocker;" for example, diphenhydramine (which is commercially available under the trademark Benadryl (Parke-Davis, Morris Plains, NJ) is an H1 blocker. Alternately, an H2 blocker such as cimetidine (which is commercially available under the trademark Tagamet (Smith Kline and French Co., Philadelphia, PA)) binds preferentially to H2 receptors.

Certain diseases are characterized by, and may be caused or aggravated by, imbalances in H1 and H2 receptor density on lymphocytes and other types of human cells. Such diseases include atopic disease [7], neoplastic disease [8], histiocytosis-X [9], autoimmune disease [10], and other diseases [11]. In order to diagnose, study, and treat such diseases it is useful to determine the existence, concentration, and biochemical affinity of H1 and H2 receptors on various types of human cells.

Although it has been recognized since 1910 that histamine causes a variety of physiological reactions, research on histamine receptors has proceeded slowly. The majority of histamine research involved detection of physiological responses, such as muscle contraction or vasodilation, which occur when tissue is contacted with histamine [12]. Some research involved the biochemical production of certain molecules, such as cyclic adenosine monophosphate (cAMP) by cells contacted with histamine [13]. In 1966, it was recognized that mepyramine, when incubated with tissue, blocked certain types of physiological responses but not other types of responses when the tissue was subsequently contacted with histamine. Based upon that result, scientists speculated that at least two types of cell membrane receptors existed, designated as H1 and non-H1 receptors [14]. In 1972, it was discovered that burimamide blocked several responses that differed from the responses blocked by mepyramine; this led to the designation of H2 receptors [15]. However, most of the research since 1972 has continued to focus upon physiological responses or cAMP stimulation [16]. There has been very little work to analyze, through biochemical binding reactions, the presence and concentration of H1 and H2 receptors on membranes [17]. Such work has suffered from serious drawbacks which hindered or prevented accurate and convenient analyses of histamine receptors.

DISCLOSURE OF THE INVENTION

This invention relates to a method for qualitatively determining whether a cell has a substantial number of histamine receptors on its surface. It may be used to classify cells into two categories, HR+ cells (which have substantial numbers of histamine receptors) and HR− cells (which do not have substantial numbers of histamine receptors). This invention also provides a method for analyzing a population of cells to determine the number, fraction, or percentage of cells that are HR+ cells. It also provides a method for separating HR+ cells from HR− cells.

This invention may be used with a variety of competitive binding techniques using substances which bind specifically to certain classes of histamine receptors, such as diphenhydramine (which preferentially binds to H1 receptors) and cimetidine (which binds preferentially to H2 receptors). Using such techniques, it is possible to classify and separate cells in categories such as H1R+, H1R−, H2R+, H2R−, and H1H2R−.

The foregoing information is useful in the characterization of cell populations, and in the study, diagnosis and treatment of a variety of diseases. In addition, it may be combined with the analytical techniques described in U.S. application Ser. No. 319,652, the teachings of which are hereby incorporated by reference, in order to provide a more detailed and accurate characterization of histamine receptors in a population of cells.

The methods of this invention comprise the use of fluorescent complexes comprising three types of molecules. At the center of each complex is a polymeric molecule, such as a globular proteinous molecule, such as albumin. A plurality of fluorescent indicator molecules is attached to the polymeric molecule. A plurality of histamine or histamine blocker molecules is also attached to the polymeric molecule. The number of histamine or histamine blocker molecules bound to each polymeric molecule may be optimized by the procedures described below in order to improve the accuracy and convenience of the analysis.

In order to perform the assay of this invention, a predetermined concentration of fluorescent complex molecules in solution is contacted with a suspension of cells. The suspension is prepared in a manner that does not cause the cells to adhere to each other. The optimal concentration, which varies depending upon several factors, may be determined by the procedures described below. The mixture is incubated at a predetermined temperature for a predetermined time. Appropriate temperature and time conditions, which vary depending upon several factors, may be determined by the procedures described below.

The incubated cells are washed to remove unbound fluorescent complexes, and analyzed by flow cytometric or other conventional techniques to determine which cells have fluorescent complexes bound to them. If desired, the flow cytometer may be equipped with a cell sorter to separate the fluorescent cells from the non-fluorescent cells.

An important aspect of this invention is the optimization of several parameters for carrying out the invention. These parameters may vary depending upon the type of cells being assayed, the type of polymeric molecule that is used, and other factors. In addition, the optimal value of any one parameter may vary, depending upon the values that are selected for the other parameters. To simplify the following description of how optimal values are selected, it is assumed that human albumin (HA) is selected as the polymeric molecule. Human albumin may be conjugated to fluorescein to produce FHA, which may be conjugated to histamine to produce FHA-his. Human albumin may also be conjugated to a histamine blocker, such as diphenhydramine or cimetidine, to create a histamine blocker complex (HBC) such as HA-dip or HA-cim.

The optimum quantity of FHA-his to be applied to a given type of cell is a function of three different variables:

(1) the number of histamine molecules that are bound to each molecule of albumin; for convenience, this is designated the "FHA-his index," which is expressed as a range of integers, e.g., from 30 to 100;

(2) the concentration of FHA-his molecules in solution, expressed in terms such as milligrams of albumin per milliliter of solution; this concentration is independent of the FHA-his index, since each FHA-his molecular complex has one molecule of albumin regardless of how many molecules of histamine are attached to it; and (3) the volume of FHA-his solution that is added to an aliquot of cells.

The concentration of FHA-his solution multiplied by the volume of FHA-his solution added to an aliquot of cells is equal to the *quantity* of FHA-his added to the cells, which can be expressed in terms such as milligrams of albumin per $10^6$ cells.

To determine the optimal range for the FHA-his index for a given type of cell, a variety of FHA-his solutions are created with a range of index levels. For each solution, a dosage-response curve is created by varying the quantity of FHA-his solution that is administered to each of several aliquots of cells. The mixture is incubated to allow the histamine molecules to become specifically bound to histamine receptors on the cells. The cells are then analyzed to determine the number or fraction of cells that have become fluorescent. For each solution, the resulting data may be plotted on a dosage-response curve. A curve may be plotted for FHA-his solutions with a range of index levels. Preferably, each dosage response curve should be based upon simultaneous incubations, in order to minimize variations in temperature, incubation time, and other parameters.

Figure 1:
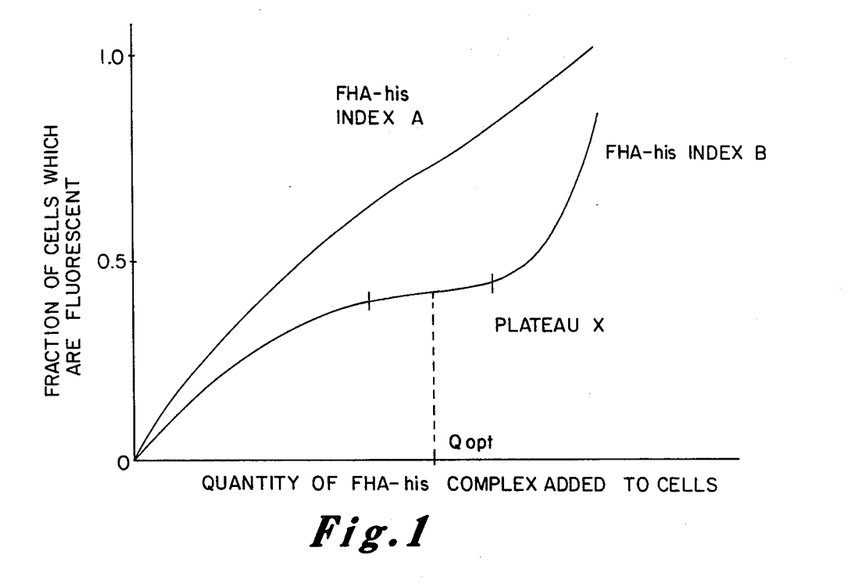

When the various dosage-response curves are plotted, one or more of the curves should have a region that is relatively flat, as shown by "Plateau X" on FIG. 1, while other curves tend to be more vertically oriented. Such a plateau is desirable since it indicates that the results of the assay are not highly sensitive to minor variations in reaction concentrations applied to the cells. The optimal FHA-his index is chosen by selecting an index which provides a curve with a large, relatively flat plateau, such as Index B as shown in FIG. 1. The optimal quantity of FHA-his is chosen to be a value which corresponds to the middle of the plateau for the chosen concentration, indicated by $Q_{opt}$ on FIG. 1.

The same procedure may be used to optimize the index of each blocker complex. For example, if cimetidine is to be used in an albumin-cimetidine HBC, it may be conjugated to FHA at a variety of index levels, incubated with cells, and analyzed by flow cytometer to develop a dosage-response curve for each index level.

Figure 2:
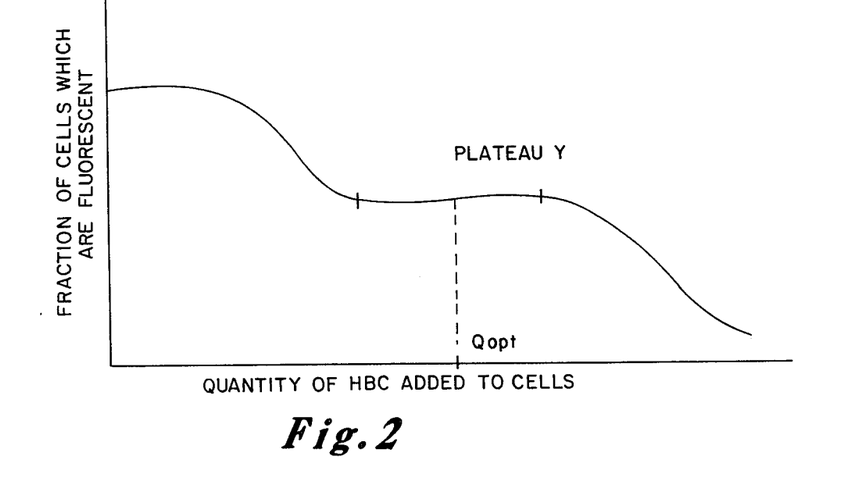

However, the procedure for selecting the proper quantity of HBC to apply to an aliquot of cells is somewhat more complex. To determine the proper concentration and volume of HBC to be used during a competitive binding assay, a suspension of cells is prepared and divided into aliquots. To each aliquot is added a predetermined, optimized amount of FHA-his, and a variable quantity of nonfluorescent HBC with an optimal index. The cells are incubated and analyzed for fluorescence, and a dosage-response curve is prepared which should resemble the idealized curve shown in FIG. 2. The existence of a large, flat plateau region, designated as Plateau Y in FIG. 2, serves as confirmation that all of the previously optimized parameters are properly balanced against each other; if no such plateau exists, one or more of the parameters should be adjusted. The optimal quantity of HBC corresponds to the center of the plateau, as shown by $Q_{opt}$ on FIG. 2.

The optimal value of each parameter depends to an extent upon the values chosen for other parameters. If an optimal value for one parameter is found which does not approximate the value selected for that parameter while other parameters were being optimized, then the optimization procedures may be repeated using the new value. This is an iterative process, which can be repeated any number of times until a full balanced set of optimized parameter is obtained.

BEST MODE OF CARRYING OUT THE INVENTION

In one preferred embodiment of this invention, a commercially available preparation of fluoresceinated human albumin (FHA) was dissolved in water. Histamine dihydrochloride was added to the solution, and 1-ethyl-3 (3-dimethylamino-propyl)-carbodiimide hydrochloride (ECDI) was added to the mixture to cause the histamine to become conjugated to the albumin. The number of histamine molecules bound to each FHA-his complex (i.e., the index of each solution) was controlled by varying the concentration of each reagent, and by varying the duration of the conjugation reaction. The resulting FHA-his complexes were then dialyzed in cold water and saline solutions; their concentrations were controlled by dilution with normal saline solution.

A suspension of human lymphocyte cells was prepared by centrifuging a sample of blood in a density gradient medium. "T-cells" were isolated from the lymphocytes by rosetting the lymphocytes with sheep erythrocytes, and resuspended in PBS. The resulting suspensions were divided into aliquots. To construct a dosage response curve for each FHA-his solution, a different volume of FHA-his solution was added to each aliquot. The aliquots were assayed in triplicate, and the results were averaged. The aliquots were incubated for 30 minutes in a 37° C. water bath. The cells were then removed from the water bath and stored on ice for no longer than 30 minutes. Immediately prior to analysis, 1.5 ml normal saline was added to each tube.

Following incubation, the cells were analyzed on a flow cytometer using 10 mW excitation at a wavelength of 488 nm from an argon ion laser source. Green fluorescence was measured in the 510–590 nm wavelength range. A minimum of 10,000 cells were analyzed for each sample. Distributions of fluorescence from individual cells were accumulated in a distribution analyzer. The controls on the fluorescence detector and scattering detector were adjusted so that FHA-his complexes would not be detected by the flow cytometer; this eliminated the need to remove the solution of unbound FHA-his molecules from the cells by filtration, washing, or other procedures.

Figure 3:
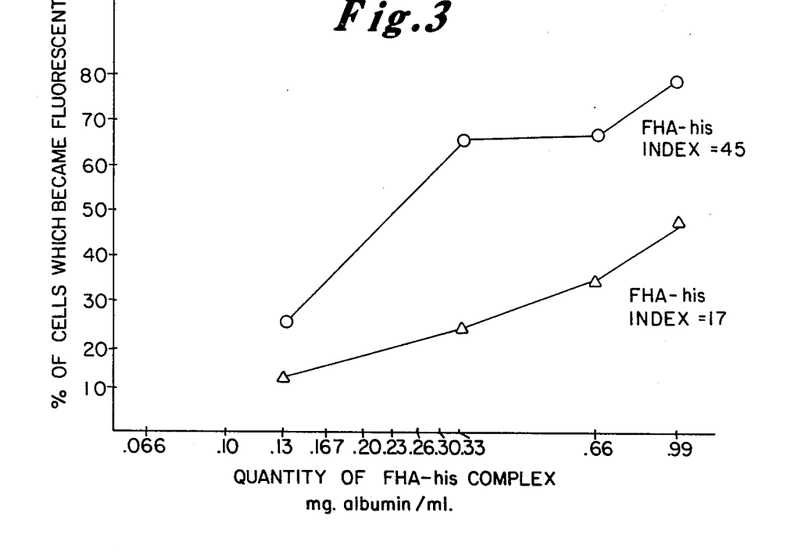

The dosage-response curves were plotted; the results of a typical experiment are shown in FIG. 3. Based upon those curves, FHA-his solutions with indexes of about 30 to about 100 were selected as opitmal; an index of about 50 was used for subsequent experiments. Several parameters determined to be optimal during this process are listed in Table I.

It was assumed that an optimal index for HA-dip and HA-cim solutions would also be in the range of 30 to 100 blocker molecules per albumin molecule. This assumption was supported by the existence of satisfactory plateaus in dosage-response curves obtained during competitive binding experiments.

Figure 4:
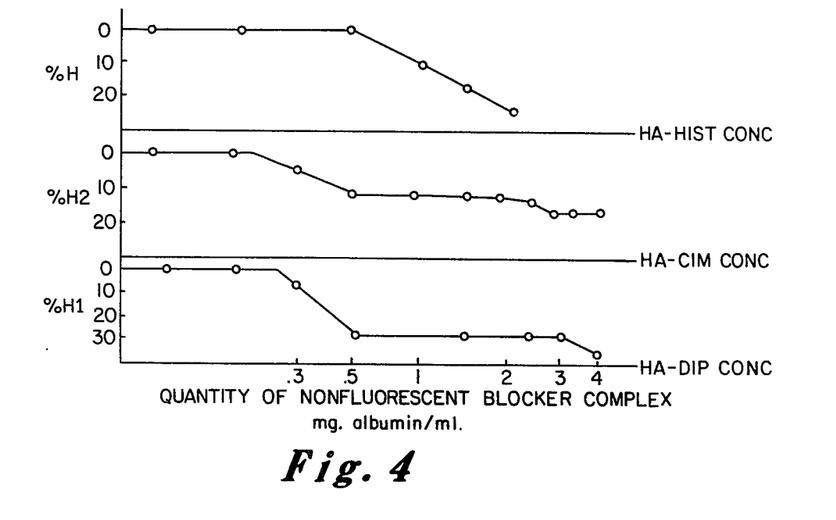

In the competitive binding experiments, the cells were prepared, incubated, and analyzed in the manner described above. To determine each dosage-response curve, each aliquot of cells was incubated with a constant quantity of FHA-his and a variable quantity of non-fluorescent HA-dip, HA-cim, or HA-his. The results of a typical experiment are shown in FIG. 4.

It is possible to prepare an assay kit to facilitate the assays of this invention. Such a kit would include one or more of the following substances:

1. a polymeric molecule, such as a globular proteinous molecule such as albumin, which has fluorescent characteristics or to which is attached at least one fluorescent molecule;
2. histamine molecules, which may be attached to the polymeric molecule described above;
3. histamine molecules, which may be attached to non-fluorescent polymeric molecules such as albumin;
4. H1 receptor blocking molecules, such as diphenlydramine, which may be attached to non-fluorescent polymeric molecules such as albumin;
5. H2 receptor blocking molecules, such as cimetidine, which may be attached to non-fluorescent molecules such as albumin.

Any substance which is known or hereafter discovered to block one or more types of histamine receptors may be useful within the scope of this invention, as may be determined through routine experimentation by those skilled in the art. For example, substances which are known to block H1 receptors, and which may be useful in this invention, include dimenhydrimate, chlorpheniramine, brompheniramine, promethazine, pyrilamine, 2-methylhistamine, 2-thiazolylethylamine, and 2-pyridylethylamine. Substances which are known to block H2 receptors, and which may be useful in this invention, include burimamide, metiamide, impromidine, dimaprit, nordimaprit, and 4-methythistamine.

A wide variety of polymeric molecules, such as proteins, hydrocarbons, or hydrocarbon derivatives, may be suitable for creating fluorescent or non-fluorescent complexes which contain histamine or histamine blocker molecules, as may be determined by those skilled in the art. The principle purpose of such complexes is to increase the affinity of the binding reaction by causing each complex to be bound multivalently, rather than univalently.

As used herein, the term "fluorescent polymeric molecules" includes polymeric molecules which are fluorescent, as well as polymeric molecules to which fluorescent molecules are attached.

TABLE 1

OPTIMAL PARAMETERS FOR
FLOW CYTOMETRIC ANALYSIS OF
HISTAMINE RECEPTORS ON HUMAN LYMPHOCYTES

| | |
|---|---|
| Type of globular protein | Human albumin |
| Molecular weight | about 60,000 daltons |

TABLE 1-continued
OPTIMAL PARAMETERS FOR
FLOW CYTOMETRIC ANALYSIS OF
HISTAMINE RECEPTORS ON HUMAN LYMPHOCYTES

| | |
|---|---|
| # of fluorescein molecules per FHA | about 5 |
| Temperature of FHA-his conjugation | Room (20° C.) |
| Duration of FHA-his conjugation | 2 hours |
| Concentrations during FHA-his conjugation (5 cc) | |
| Albumin | 50 mg |
| Histamine dihydrochloride | 150 mg |
| ECDI | 300 mg |
| # of histamine molecules per FHA-his | about 30 to 100, preferably 50 |
| Concentration of FHA-his, mg albumin per ml | about 3.3 |
| Volume and concentration of cells before addition of FHA-his | 50 ul; about $2 \times 10^7$ cells/ml |
| Volume of FHA-his added to cells | 10 ul |
| Temperature of reaction | 37° C. |
| Duration of reaction | 30 min. |

EXAMPLES

Example 1

Preparation and Fixation of Lymphocytes

Human lymphocytes were separated from blood samples collected in preservative-free heparin, by centrifugation using Lymphocyte Separation Medium (Bionetics Lab Products, Kensington, MD.). T cells were isolated by rosetting lymphocytes with sheep erythrocytes. Some of the cells were fixed by suspension in phosphate-buffered normal saline (PBS) containing 1% formaldehyde. Fresh cells were used within six hours of preparation; fixed cells were stored at 4° C. until use.

Example 2

Preparation of FHA-his Complexes

Fluoresceinated human albumin (FHA) was obtained from Cappel Laboratories (Cochranville, PA). Each molecule of albumin is labeled with approximately five molecules of fluorescein. The FHA was dissolved in water at a concentration of 10 mg/ml. Varying quantities of histamine dihydrochloride (Sigma Chemical Co., St. Louis MO.) and a coupling agent, 1-ethyl-3 (3-dimethylamino-propryl)-carbodiimide hydrochloride (ECDI) (Sigma Chemical Co.) were added to 5 cc of the FHA solution. During this process, the ratio of ECDI to histamine (mg/mg) was maintained at 2:1; the ratio of histamine to albumin (mg/mg) was varied from about 1:1 to about 10:1.

The conjugation of histamine dihydrochloride to albumin was allowed to proceed for two hours at room temperature in the dark. A tritiated histamine tracer (New England Nuclear, Boston MA.) was added to each batch to enable monitoring of the amount of histamine conjugated to FHA. Following the conjugation reaction, each FHA-his solution was dialyzed twice against a 300-fold volume of water, and once against a 300-fold of normal saline, to remove unconjugated histamine and ECDI. All dialyses were performed for 90 minutes at 4° C. in the dark. Following the last dialysis, the solution was adjusted to a final albumin concentration of 3.3 mg/ml in normal saline.

Example 3

Preparation of Histamine Blocker Complexes (HBC)

In order to prepare non-fluorescent histamine blocker complexes (HBC), a solution of human albumin, 25 mg/ml in normal saline, was obtained from Boston University Hospital Pharmacy. Phosphate buffer was added to the HA solution for certain uses. Based upon earlier optimization work (described below) involving FHA-his complexes, it was assumed that an index of about 50 to 100 blocker molecules per albumin molecule was an optimal value. To obtain HBC solutions with that index range, 1 gram of either diphenhydramine hydrochloride (Sigma Chemical Co.) or cimetidine (Smith Kline and French Laboratories, Philadelphia PA), and 2 g ECDI were added to 4 ml of the HA solution (100 mg albumin). The conjugation reactions were allowed to proceed for two hours at room temperature, followed by dialysis twice against a 300-fold volume of water; each dialysis was done for 90 minutes at 4° C. Following the second dialysis, the solution was lyophilized (freeze-dried) and reconstituted with normal saline to a final albumin concentration of 4.5 mg/ml.

Control human albumin (HA) without histamine or histamine blocker was reacted with ECDI and processed in a manner identical to the HBC complexes.

Example 4

Incubation of Cells with Non-fluorescent Blockers and FHA-his

A cellular suspension, prepared as described in Examples 1 and 2, was suspended in PBS containing 2 mmol $CaCl_2$ and 1 mmol $MgSO_4$ (PBS/CaMg) at a concentration of $1 \times 10^7$ cells/ml. This suspension was divided into 50 ul aliquots in plastic tubes.

For those aliquots used in competitive binding determinations, 25 ul of non-fluorescent control albumin, Ha-dip, HA-cim or HA-his was added to each aliquot; the mixture was incubated for 15 minutes at 37° C. 10 ul of FHA-his was then added, and the volume of the solutions was brought to 100 ul with PBS/CaMg. The cells were then incubated for 60 minutes at 37° C. in a water bath, then removed and stored on ice for no longer than 30 minutes.

For those aliquots that were subjected to FHA-his labeling without competitive binding, 10 ul of FHA-his was added to each aliquot, the final volume was brought to 100 ul with normal saline, and the cells were incubated for 60 minutes in a 37° water bath, at which time they were removed and stored on ice for no longer than 30 minutes.

Example 5

Flow Cytometric Analysis

Immediately prior to analysis, 1 ml of normal saline was added to each tube that was processed as described above. The cells were analyzed on a Bio/Physics (now Ortho Instruments) Cytoflurograf Model No. 4800A, using 10 mw excitation at 488 nm from an argon ion laser source. Green fluorescence was measured in the 530–590 nm wavelength range. In order for a cell to be counted, a positive reading is required at the fluorescence detector and at the light scattering detector; by adjusting the controls on the light scattering detector, it is possible to avoid counting FHA-his molecules in solution unless they are attached to a cell. This prevents the need for removing the unbound FHA-his molecules from the solution. A minumum of 10,000 cells were analyzed for each sample. Laser power, photomultiplier tube gain, and pulse height analyzer display settings were kept constant for all samples in an experiment. Distributions of fluoresence for individual cells were displayed on a Bio/Physics Model No. 2101 Distrubition Analyzer.

Figure 5:
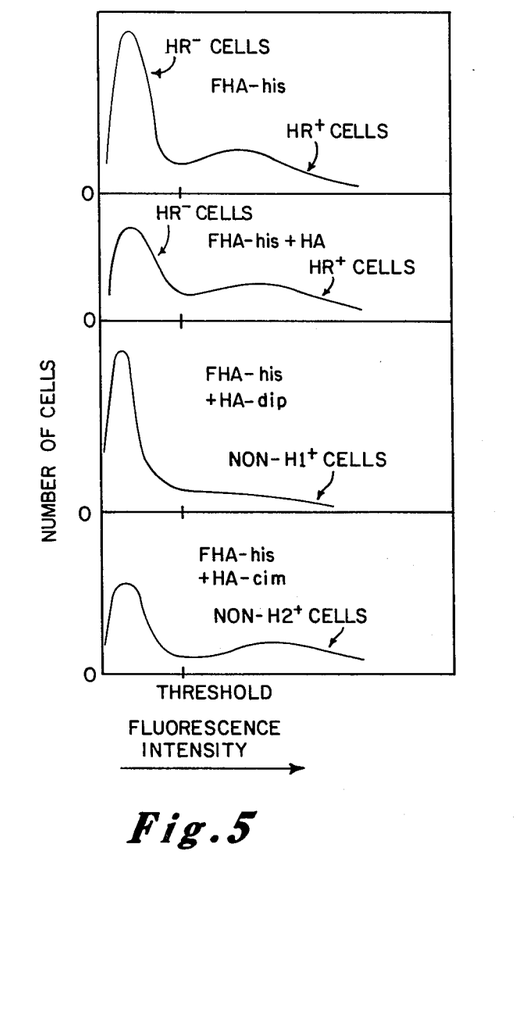

The results from a typical experiment are shown in FIG. 5. As indicated in that figure, a large peak exists in a range of low fluorescence intensity; a substantially broader peak exists over a wider range of higher fluorescence intensity. By visual analysis of this curve, it is possible to divide the two peaks into different regions, by determining a fluorescence threshold level. Those cells with fluorescence intensity less than the threshold level are regarded as lacking in substantial numbers of histamine receptors, i.e., HR−. Those cells with fluorescence intensity greater than the threshold level are regarded as having substantial numbers of histamine receptors, i.e., HR+. It is not necessary, for the purposes of this invention, to determine the number of histamine receptors comprising the threshold level.

From each analysis, the percentage of cells in the higher fluorescent intensity ranger was calculated automatically, and used as a data point to construct a dosage-response curve such as the curves shown in FIGS. 3 and 4.

Example 6

Determination of Optimal Labeling and Competitive Binding Parameters

Dosage-response curves were prepared, using the data points obtained by the methods described in Example 5, for FHA-his solutions with a range of index values. Two dosage-response curves from typical experiments are indicated in FIG. 3. Based upon these results, it was determined that solutions with an FHA-his index of approximately 30-100 histamine molecules per albumin molecule were optimal for use with human T cells. It was also determined that a quantity of FHA-his complex equal to approximately 0.33 mg albumin/$10^6$ cells was an optimal volume FHA-his solution. These levels were used during subsequent experiments.

Based upon data points obtained from the competitive binding procedures described in Example 4, analyzed as described in Example 5, a dosage-response curve was obtained for HA-dip and HA-cim solutions. These solutions were assumed to have an optimal index of between about 30 and about 100, based upon the previous optimization involving FHA-his complexes; solutions with an index believed to be about 100 were used. The results of these curves are shown in FIG. 4. Based upon these dosage-response curves, dosages of 1.1 mg albumin/$10^6$ cells were determined to be optimal.

EQUIVALENTS

Those skilled in the art will recognize, or be able to ascertain using no more than routine experimentation, numerous equivalents to the specific procedures described herein. Such equivalents are considered to be within the scope of this invention, and are covered by the following claims.

REFERENCES

1. See, e.g., T. O. Yellin, Editor, *Histamine Receptors*, SP Medical and Scientific Books, New York (1979).
2. See, e.g., M. E. Parsons et al, "3-[4(5)-Imidazolyl] propylguanidine—a Partial Agonist at Histamine H2 Receptors," *Agents Actions* 5: 464 (1975).
3. See, e.g., J. W. Black et al, "Metiamide—an Orally Active Histamine H2 Receptor Antagonist," *Agents Actions* 3: 133-137 (1973).
4. See, e.g., M. Osband et al, "Solubilization, Separation, and Partial Characterization of Histamine H1 and H2 Receptors From Calf Thymocyte Membranes", *J. Biol. Chem.* 254: p. 9970-9972 (1979).
5. See, e.g., R. R. Schade, "How Physicians Use Cimetidine", *N. Eng. J. Med.* 304: p. 1281-1284 (1981).
6. See, e.g., A. S. F. Ash et al, "Receptors Mediating Some Actions of Histamine," *Brit. J. Pharmacol. Chemotherap.* 27: p. 427-439 (1966).
7. See, e.g., J. D. Martinez et al, "Non-specific Suppressor Cell Function in Atopic Subjects", *J. Am. Clin. Imm.* 64: p. 485 (1979).
8. See, e.g., B. Schechter, "Enhancing Lymphocytes in Spleen of Tumor-bearing Mice", *Int. J. Cancer* 20: p. 239 (1977).
9. M. E. Osband, "Histiocytosis-X", *N. Eng. J. Med.* 304: p. 146-153 (1981).
10. W. DeCock et al, "Histamine Receptor-bearing T Lymphocytes in Patients with Allergy, Autoimmune Disease, or Recurrent Infection", Clin. Immunol. Immunopath. 11: p. 1 (1978).
11. See, e.g., A. Gupta, "Markers of Human Lymphocyte Subpopulations in Primary Immunodeficiency and Lymphoproliferative Disorders", *Semin. Hemat.* 17: p. 1 (1980).
12. See, e.g., M. A. Beaven, *Histamine, Its Role in Physiological and Pathological Processes*, p. 36-51 (S. Carger, Basel, Switzerland, 1978).
13. See, e.g., H. Shimizu et al, "The Effect of Histamines and Other Compounds on the Formation of AMP in Slices from Cerebral Cortex", *J. Neurochemistry* 17: p. 441-444 (1970).
14. See Ash et al, supra note 6.
15. J. W. Black et al, "Definition and Antagonism of Histamine H2 Receptors", *Nature* 236: p. 385-390 (1972).
16. See Yellin, supra note 1.
17. S. J. Hill et al, "Specific Binding of $^3$H-mepyramine to Histamine H1 Receptors in Intestinal Smooth Muscle", *Nature* 270: p. 361-363 (1977); W. P. Burkard, "Histamine H2 Receptor Binding with $^3$H-cimetidine in Brain", *Euro. J. Pharmacol.* 50: p. 449-450 (1978).

We claim:

1. A method for analyzing cells to determine the fraction which have a substantial number of receptors for histamine on their surface comprising the following steps:
    a. preparing a suspension of cells or cell fragments in a buffer solution containing calcium and magnesium ions in a manner that does not cause said cells or fragments to adhere to each other;
    b. contacting said suspension of cells or cell fragments with a solution containing a molecular complex comprising fluorescent protein or peptide polymeric molecules to which are attached a plurality of molecules that specifically bind to histamine receptors, the concentration of the complex and the index of the complex being such that the fraction of cells exhibiting fluorescence does not change substantially with minor variations in the concentration of the complex; and c. analyzing said cells or fragments to determine the number or fraction of cells or fragments that have a relatively high level of fluorescence, whereby the level of fluorescence is related to the quantity of receptors for histamine on the cell surface.

2. A method for analyzing cells comprising the following steps:
   a. preparing a suspension of cells or cell fragments in a buffer solution containing calcium and magnesium ions in a manner that does not cause said cells or fragments to adhere to each other;
   b. dividing said suspension into at least two aliquots;
   c. contacting at least one first aliquot with a first solution comprising molecules that specifically bind to H1 receptors, and with a second solution comprising fluorescent protein or peptide polymeric molecules to which are attached a plurality of molecules that specifically bind to histamine receptors, the concentration of the complex and the index of the complex being such that the fraction of cells exhibiting fluorescence does not change substantially with minor variations in the concentration of the complex;
   d. contacting at least one second aliquot with a solution comprising the fluorescent protein or peptide polymeric molecules to which are attached a plurality of molecules that specifically bind to histamine receptors;
   e. incubating said aliquots with said solutions at an appropriate temperature for an appropriate time; and
   f. analyzing said aliquots to determine the number or fraction of cells or fragments in each aliquot that have a relatively high level of fluorescence, whereby the level of fluorescene is related to the number of H2 receptors on the cell surface.

3. A method for analyzing cells comprising the following steps:
   a. preparing a suspension of cells or cell fragments in a buffer solution containing calcium and magnesium ions in a manner that does not cause said cells or fragments to adhere to each other;
   b. dividing said suspension into at least two aliquots;
   c. contacting at least one first aliquot with a first solution comprising molecules that specifically bind to H2 receptors, and with a second solution comprising fluorescent protein or peptide polymeric molecules that specifically bind to histamine receptors, the concentration of the complex and the index of the complex being such that the fraction of cells exhibiting fluorescence does not change substantially with minor variations in the concentration of the complex;
   d. contacting at least one second aliquot with a solution comprising the fluorescent proetin or peptide polymeric molecules to which are attached a plurality of molecules that specifically bind to histamine receptors;
   e. incubating said aliquots with said solutions at an appropriate temperature for an appropriate time; and
   f. analyzing said aliquots to determine the number or fraction of cells or fragments in each aliquot that have a relatively high level of fluorescence whereby the level of fluorescence is related to the number of H1 receptors on the cell surface.

4. A method of claims 1, 2 or 3 wherein said molecules that specifically bind to histamine receptors are selected from the following group: histamine and substituted histamine.

5. A method of claims 1, 2, or 3 wherein said fluorescent polymeric molecules comprise globular proteinous molecules to which are attached a plurality of fluorescent molecules.

6. A method of claims 1, 2, or 3 wherein said aliquots are incubated for at least about 30 minutes at a temperature of at least about 30° C.

7. A method of claims 2 or 3 wherein said first aliquot is incubated with said first solutions at an appropriate temperature for an appropriate time before said first aliquot is contacted with said second solution.

8. A method of claim 7 wherein said appropriate temperature is at least about 30° C. and said appropriate time is at least about 10 minutes.

9. A method of claims 1, 2, or 3 wherein between about 30 and about 100 of said molecules that specifically bind to histamine receptors are attached to each fluorescent protein or peptide polymeric molecule.

10. A method of claim 2 wherein said first solution comprises protein or peptide polymeric molecules to which are attached a plurality of molecules that specifically bind to H1 receptors.

11. A method of claim 3 wherein said first solution comprises protein or peptide polymeric molecules to which are attached a plurality of molecules that specifically bind to H2 receptors.

12. A method of claims 2 or 10 wherein said molecules that specifically bind to H1 receptors are selected from the following group: diphenhydramine, dimenhydrimate, chlorpheniramine, brompheniramine, promethazine, pyrilamine, 2-methylhistamine, 2-thiazolylethylamine, and 2-pyridylethylamine.

13. A method of claims 3 or 11 wherein said molecules that specifically bind to H2 receptors are selected from the following group: cimetidine, burimanide, metiamide, impromidine, dimaprit, nordimaprit, and 4-methythistamine.

14. An assay kit for analyzing histamine receptors, comprising a molecular complex comprising fluorescent protein or peptide polymeric molecules to which are attached a plurality of molecules that specifically bind to histamine receptors, said complex having an index such that when specified concentration of the complex is contacted with cells bearing histamine receptors on their surface, the fraction of cells exhibiting fluorescence is independent of minor variations in the concentration of complex.

15. An assay kit for analyzing histamine receptors, comprising a molecular complex comprising fluorescent protein or peptide polymeric molecules to which are attached a plurality of molecules that specifically bind to histamine receptors, said complex having an index such that when specified concentration of the complex is contacted with cells bearing histamine receptors on their surface, the fraction of cells exhibiting fluorescence is independent of minor variations in the concentration of complex, and either or both of the following elements:
   a. molecules that specifically bind to H1 receptors; and
   b. molecules that specifically bind to H2 receptors.

16. An assay kit of claim 15 wherein said molecules that specifically bind to H1 receptors comprise a plurality of said molecules attached to said polymeric molecules.

17. An assay kit of claim 16 wherein said molecules that specifically bind to H2 receptors comprise a plurality of said molecules attached to said polymeric molecules.

18. A composition of matter comprising a protein or peptide polymeric molecule to which is attached between about 30 to about 100 molecules of histamine or substituted histamine.

19. A composition of matter of claim 18 wherein said polymeric molecule comprises a globular protein.

20. A composition of matter comprising a protein or peptide polymeric molecule to which is attached a plurality of cimetidine molecules.

21. A composition of matter comprising a protein or peptide polymeric molecule to which is attached a plurality of diphenhydramine molecules.

22. A composition of claims 18, 20 or 21 wherein a plurality of fluorescent molecules are attached to said polymeric molecules.

23. A method of determining the fraction of a population human lymphocytes that have a substantial number of receptors for histamine on their surface comprising the following steps:
  a. preparing a suspension of lymphocytes in a buffer solution containing about 2 mmol $CaCl_2$ and about 1 mmol $MgSO_4$ in a manner that does not cause the lymphocytes to adhere to each other;
  b. contacting the suspension of lymphocytes with a solution containing a molecular complex comprising fluoresceinated human albumin and about 30 to about 100 molecules of histamine or substituted histamine;
  c. analyzing the lymphocytes to determine the fraction of lymphocytes that have a high level of fluorescence whereby the level of fluorescence is related to the quantity of receptors for histamine on the surface of the lymphocytes.

* * * * *